United States Patent
Wang

(10) Patent No.: US 11,913,879 B2
(45) Date of Patent: Feb. 27, 2024

(54) NON-DISPERSIVE INFRARED SENSOR

(71) Applicant: Focus Universal Inc., Ontario, CA (US)

(72) Inventor: Desheng Wang, Diamond Bar, CA (US)

(73) Assignee: Focus Universal Inc., Ontario, CA (US)

(*) Notice: Subject to any disclaimer, the term of this patent is extended or adjusted under 35 U.S.C. 154(b) by 85 days.

(21) Appl. No.: 17/749,982

(22) Filed: May 20, 2022

(65) Prior Publication Data

US 2022/0373456 A1 Nov. 24, 2022

Related U.S. Application Data

(60) Provisional application No. 63/190,934, filed on May 20, 2021.

(51) Int. Cl.
*G01N 21/3504* (2014.01)
*G01N 33/00* (2006.01)
*G01N 21/31* (2006.01)

(52) U.S. Cl.
CPC ..... *G01N 21/3504* (2013.01); *G01N 33/0022* (2013.01); *G01N 2021/3125* (2013.01); *G01N 2021/3188* (2013.01)

(58) Field of Classification Search
CPC ........... G01N 21/3504; G01N 33/0022; G01N 2021/3125; G01N 2021/3188; G01N 2021/3137; G01N 2201/0806
See application file for complete search history.

(56) References Cited

U.S. PATENT DOCUMENTS 11,385,172 B2 * 7/2022 Tröllsch ............... G01N 21/031

* cited by examiner

*Primary Examiner* — David P Porta
*Assistant Examiner* — Meenakshi S Sahu
(74) *Attorney, Agent, or Firm* — Knobbe, Martens, Olson & Bear, LLP

(57) ABSTRACT

Disclosed is a sensor and method for detecting one or more gasses in a sample. The sensor includes two sample tube sections, which allow for a larger sample, and correspondingly, more accurate measurement. Having two sample tube sections increases the total length of the sample path. However, placing the sample tube sections in parallel allows for the performance of the sensor to be enhanced, but the footprint of the sensor to remain unchanged. Light pipe material may be used to transport the light between sample tube sections. Further, light pipe material may be used to move the IR lamp away from the first filter tube section, reducing problems in the thermopile by dissipating heat from the IR lamp away from the sample tube section.

20 Claims, 4 Drawing Sheets

NON-DISPERSIVE INFRARED SENSOR

CROSS-REFERENCE TO RELATED APPLICATIONS

The present application claims the benefit of priority to U.S. Provisional Patent Application No. 63/190,934, filed May 20, 2021, the disclosure of which is hereby incorporated by reference in its entirety. Any and all applications for which a foreign or domestic priority claim is identified in the Application Data Sheet as filed with the present application are hereby incorporated by reference under 37 CFR 1.57.

FIELD

The present invention relates to sensors which detect the presence of a gas.

BACKGROUND

In state-of-the-art non-dispersive infrared (NDIR) sensors, an infrared (IR) lamp directs waves of light through a tube filled with a sample of air toward an optical filter in front of an IR light detector. The IR light detector measures the amount of IR light that passes through the optical filter. The remainder of the IR light has been absorbed by the gas in the sample. One example of a NDIR sensor is a NDIR sensor to detect the presence of carbon dioxide ($CO_2$). The band centered on a 4.2 micron wavelength of IR radiation produced by a lamp in a $CO_2$ NDIR sensor is very close to the 4.26 micron absorption band of $CO_2$. Because the IR spectrum of $CO_2$ is unique, matching the light source wavelength serves as a signature or "fingerprint" to identify the $CO_2$ molecule.

The IR lamp produces light which passes through a length of the tube, the $CO_2$ gas molecules absorb the specific band of IR light while letting other wavelengths of light pass through. At the detector end the remaining light hits an optical filter that absorbs every wavelength of light except the 4.2 micron wavelength absorbed by $CO_2$ molecules in the air sample tube. Finally, an IR detector reads the remaining amount of 4.2 micron light that was not absorbed by the $CO_2$ molecules or the optical filter.

The difference between the amount of light radiated by the IR lamp and the amount of IR light received by the detector is measured. Since the difference is the result of the light being absorbed by the $CO_2$ molecules in the air inside the tube, it is directly proportional to the number of $CO_2$ molecules in the air sample tube. All measurements start out as analog micro-voltages. While some sensors output this as an analog voltage or 4-20 mA signal, some also include an analog to digital converter on the sensor PCB that converts the voltages into serial or RS-485 output. Serial output is especially useful for using NDIR $CO_2$ sensors with Arduino or Raspberry Pi micro controllers.

A continuing problem in state-of-the-art NDIR sensors has been size. As discussed in the example above, there must be a tube to capture the sample. The necessity of this tube to capture the sample and contain the IR spectrum light in combination with the fact that a minimum length is necessary to get a quality detection means that it is difficult to reduce the size of the sensor below the optimum length for the tube, causing a size/performance tradeoff. Thus, the optimum sensor will have a long tube length essentially precluding a small overall sensor size.

Another problem with state-of-the-art NDIR sensors is that the IR lamp heats the sample tube. In addition to the obvious problem of heat itself impacting the operation of the circuit components on the circuit board of the NDIR sensor, the heat generated by the IP lamp located on one end of the sample tube may have other negative effects. Many NDIR sensors uses a large number of thermocouples connected either in series or parallel to create a thermopile. The output voltage of the series-connected thermocouples depends on the temperature difference between the thermocouple junctions and the reference junction. If the reference junction is heated by the lamp, there can be problems with the output voltage. This results in incorrect data fed from the detector, and can lead to false negative detections.

For the foregoing reasons, there is a need for a sensor which optimizes accuracy in detection, but also comes in a small package.

SUMMARY

In some embodiments, a sensor for detecting the presence of one or more gasses includes an IR lamp that generates light in the IR spectrum. The sensor includes a first light pipe section having a first end portion and a second end portion. The first end portion abuts the IR lamp and the first light pipe section passes the light through from the first end portion to the second end portion. The sensor includes a first sample tube section receiving light from the first light pipe section. The first sample tube section has a first interior containing a first sample. The first sample includes a mix of gases from the local atmosphere. The IR spectrum light passes through the interior of the first sample tube section to a second end portion of the first sample tube section. The sensor includes a second light pipe section that has an arcuate shape so that a first end and a second end of the second light pipe section face the same direction. The first end portion of the second light pipe section can be located adjacent to a second end portion of the first sample tube section. The second light pipe section can receive the light at the second end portion of the first sample tube section and transmit the light from the first end portion to a second end portion. The sensor can include a second sample tube section with a first end portion and a second end portion. The first end portion of the second sample tube section can be located adjacent to the second end portion of the second light pipe section. The first end portion of the second sample tube section can receive the light from the second end of the second light pipe section. The second sample tube section can have a second interior containing a second sample. The second sample can include the mix of gases from the local atmosphere, such that the light passes through the interior of the second sample tube section to a second end portion of the second sample tube section. The sensor can include a first filter located at the second end portion of the second sample tube section. The first filter can bandpass a band of IR spectrum light centered on a wavelength that is indicative of the presence of a gas in the mix of gases from the local atmosphere. The sensor can include a first detector located behind to the first filter. The detector can be configured to detect the amount of IR spectrum light in the band of IR spectrum light.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

The detailed description set forth below in connection with the appended drawings is intended as a description of the presently preferred embodiment of a sensor for detecting various gasses which may be present in a local atmosphere, and is not intended to represent the only form in which it can be developed or utilized. The description sets forth the functions for developing and operating the system in connection with the illustrated embodiments. It is to be understood, however, that the same or equivalent functions may be accomplished by different embodiments that are also intended to be encompassed within the scope of the present disclosure. It is further understood that the use of relational terms such as first, second, distal, proximal, and the like are used solely to distinguish one from another entity without necessarily requiring or implying any actual such relationship or order between such entities.

Figure 1:
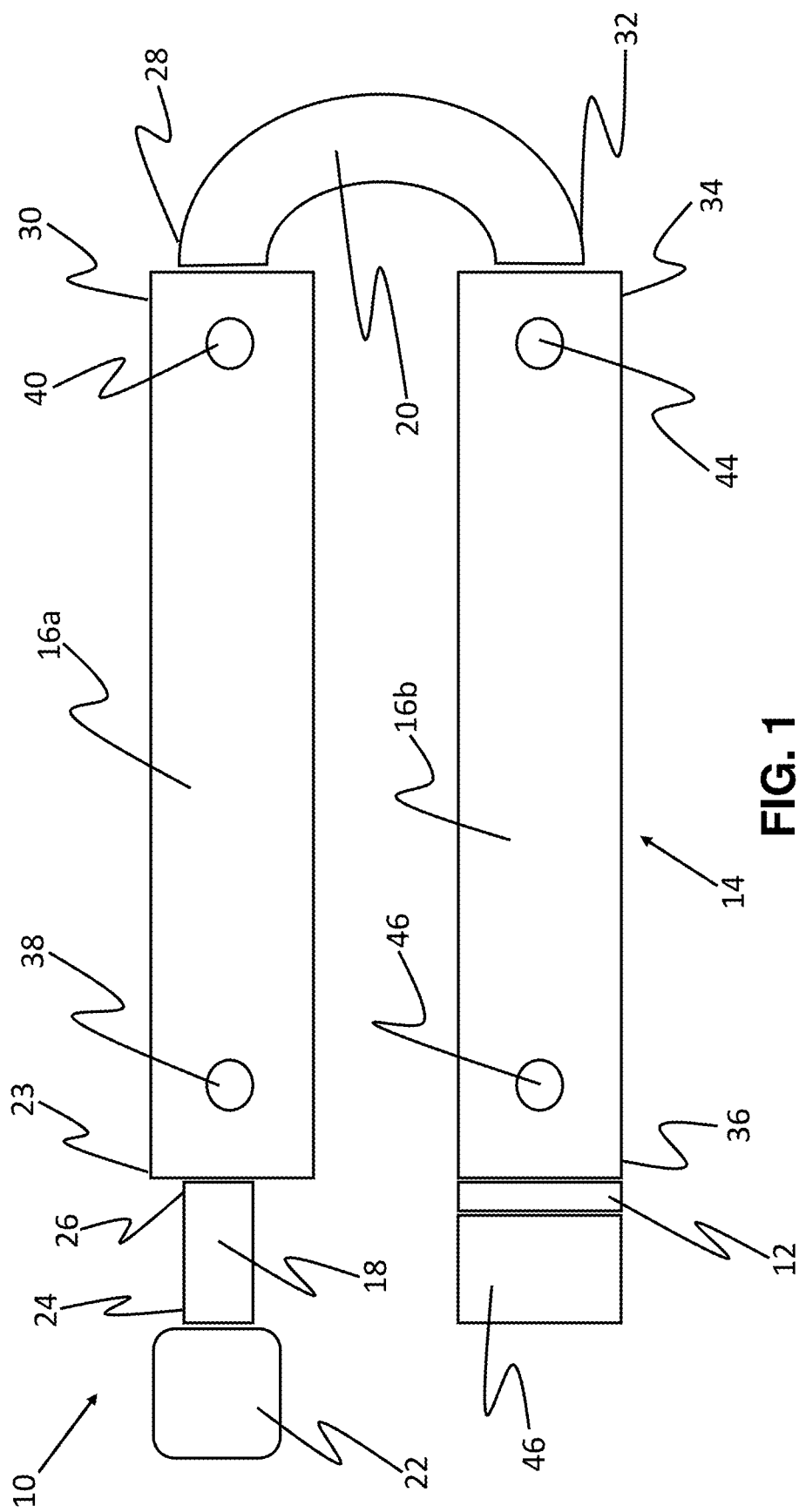
FIG. 1 shows a schematic diagram of a portion of the sensor.

FIG. 1 illustrates an overview of a portion of the gas detection sensor 10 according to the present invention. The gas detection sensor 10 may be used to detect a number of different gasses depending on the filter 12 used by the sensor.

The gas detection sensor 10 may include a plurality of components. Collectively, the components may allow the sensor 10 to generate light in the IR spectrum, guide the emission of the IR spectrum light through a sample, and then filter and detect the emission after passing through the sample.

An IR lamp 22 may be the source of the IR emission. The IR lamp 22 may be located on a first end portion 24 of a first section 18 of light pipe. The closer the light pipe first section 18 is placed to the IR lamp 22, the more efficiently the light pipe will operate. In preferred embodiments, the first section 18 of the light pipe abuts the IR lamp 22. A light pipe body extends between the first end portion 24 and a second end portion 26 of the first section 18. They body may have a cylindrical cross section. Alternatively, the body may have a square cross section, a rectangular cross section, an octagonal cross section or any cross section which allows for the efficient transmission of the IR source light.

The gas detection sensor 10 may include a sample tube 14 of two sections 16a, 16b. The second end portion 26 of the first section 18 of light pipe may be located substantially at a first end portion 23 of a first section 16a of the sample tube. Thus, the first section 18 of light pipe may be located entirely before the first section of sample tube 16a. Alternatively, a second end portion 26 may be partially located within the first section 16a of the sample tube.

Figure 2:
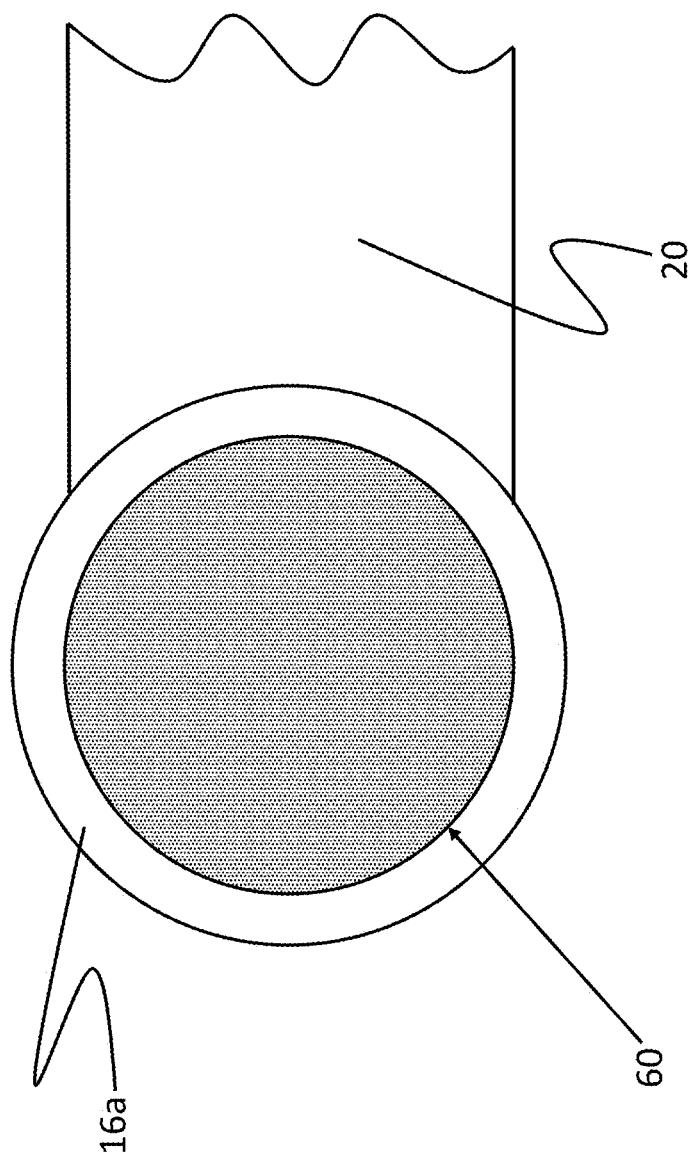
FIG. 2 shows a view of the interior of the first sample tube section and the second light pipe section.

As shown in FIGS. 1 and 2, the first sample tube section 16a may be a hollow tube. That is, the first section 16a may have a first end portion 23. The first end portion 23 may include the face of a cylindrical wall forming a body of the tube. The face of the cylindrical wall may define a circular first end opening. The cylindrical wall may also define an interior 60 of first section 16a of the sample tube. The first sample tube section 16a may include a first aperture 38 which allows gas to enter the interior of the first sample tube section 16a. The first aperture 38 may be located on the first end portion 23 of the first section 16a. The first aperture 38 may be an opening in the cylindrical wall of the first section 16a. The first section may further have a second aperture 40 which allows gas to pass from the interior of the first section 16a to an exterior of the first section 16a. The second aperture 40 may be located near a second end portion 30 of the first section 16a. Similar to the first aperture 38, the second aperture 40 may be an opening in the cylindrical wall of the first section 16a. That is, a portion of the material of the cylindrical wall may be removed to place the interior of the first section 16a in fluid communication with the exterior of the first section 16a.

As shown in FIGS. 1 and 2, a second light pipe section 20 may be located between the first sample tube section 16a and second sample tube section 16b. The second light pipe section 20 may be curved. The second light pipe section 20 may be made from a rigid material. Alternatively, the second light pipe section 20 may be made from a flexible material. A first end portion 28 of the curved second light pipe section 20 may be substantially located near or overlapping a second end portion 30 of the first sample tube section 16a. A second end portion 32 of the curved second light pipe section 20 may be substantially located at a first end portion 34 of the second sample tube section 16b. As with the first light pipe section 18, end portions 28, 32 of the second light pipe section 20 may be located partially within the sample tube sections 16a, 16b. An outer circumference of the second light pipe section 20 may be substantially equal to an inner diameter of the cylindrical wall of the first sample tube section 16a.

The second light pipe section 20 may be rigid or flexible. If it is rigid it may be formed in a 'u' shape of predetermined dimensions. If the second light pipe section 20 is flexible, the section may be cut to length, and adapters attached to connect the flexible light pipe securely to the second end portion 30 of the first sample tube section 16a, and the first end portion 34 of the second sample tube section 16b.

Figure 3:
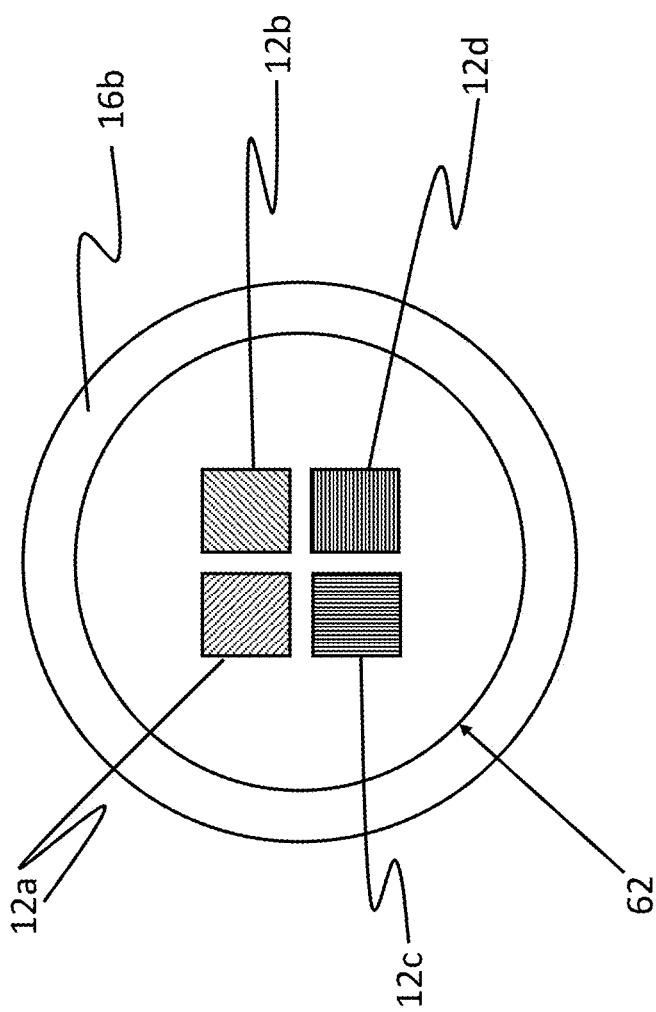
FIG. 3 shows a view of the interior of the second sample tube section and a plurality of decoder windows covered by filters.

As shown in FIGS. 1 and 3, the second sample tube section 16b may be similar to the first sample tube section 16a. The second light pipe section 20 directs the light from the second end portion 30 of the first sample tube section 16a to the first end portion 34 of the second sample tube section 16b. The second sample tube section 16b may include a hollow tube. The first end portion 34 of the second sample tube section 16b may include the face of a cylindrical wall forming body of the tube. The face of the cylindrical wall may define a circular first end opening. The cylindrical wall may also define an interior 62 of first sample tube section 16a. The second sample tube section 16b may include a first aperture 44 which allows gas to enter the interior of the sample tube. The first aperture 44 may be located on the first end portion 34 of the second sample tube section 16b. The first aperture 38 may be an opening in the cylindrical wall of the second sample tube section 16b. The second sample tube section 16b may further have a second aperture 46 which allows gas to pass from the interior 62 of the second sample tube section 16b to an exterior of the second sample tube section 16b and back in to atmosphere. The second aperture 46 may be located near a second end portion 36 of the second sample tube section 16b. Similar to the first aperture 44, the second aperture 46 may be an opening in the cylindrical wall of the second sample tube section 16b. That is, a portion of the material of the cylindrical wall may be removed to place the interior of the second sample tube section 16b in fluid communication with the local atmosphere exterior to the second sample tube section 16b.

The filter 12 may be located at or overlapping a second end portion 36 of the second sample tube section 16b. The filter 12 may abut the second end portion 36 of the second sample tube section 16b in order to filter most effectively. The IR detector 42 may be located behind the filter 12. The IR detector 42 may abut the filter in order to most effectively detect the amount of light not absorbed by the sample.

The filter 12 may filter out a narrow band spectral region which overlaps with the absorption region of the gas of interest. The filter 12 may be interchangeable. For example, the filter 12 may be placed in a frame which secures the filter in an optimum location. Based on the filter, the sensor 10 may detected the presence of a particular gas. If the filter were changed, a different gas may be detected, the filter will bandpass a band centered on a different wavelength. The wavelength will correspond to the peak IR absorption wavelength of the gas to be detected, and thus may be termed a detection wavelength.

Figure 4:
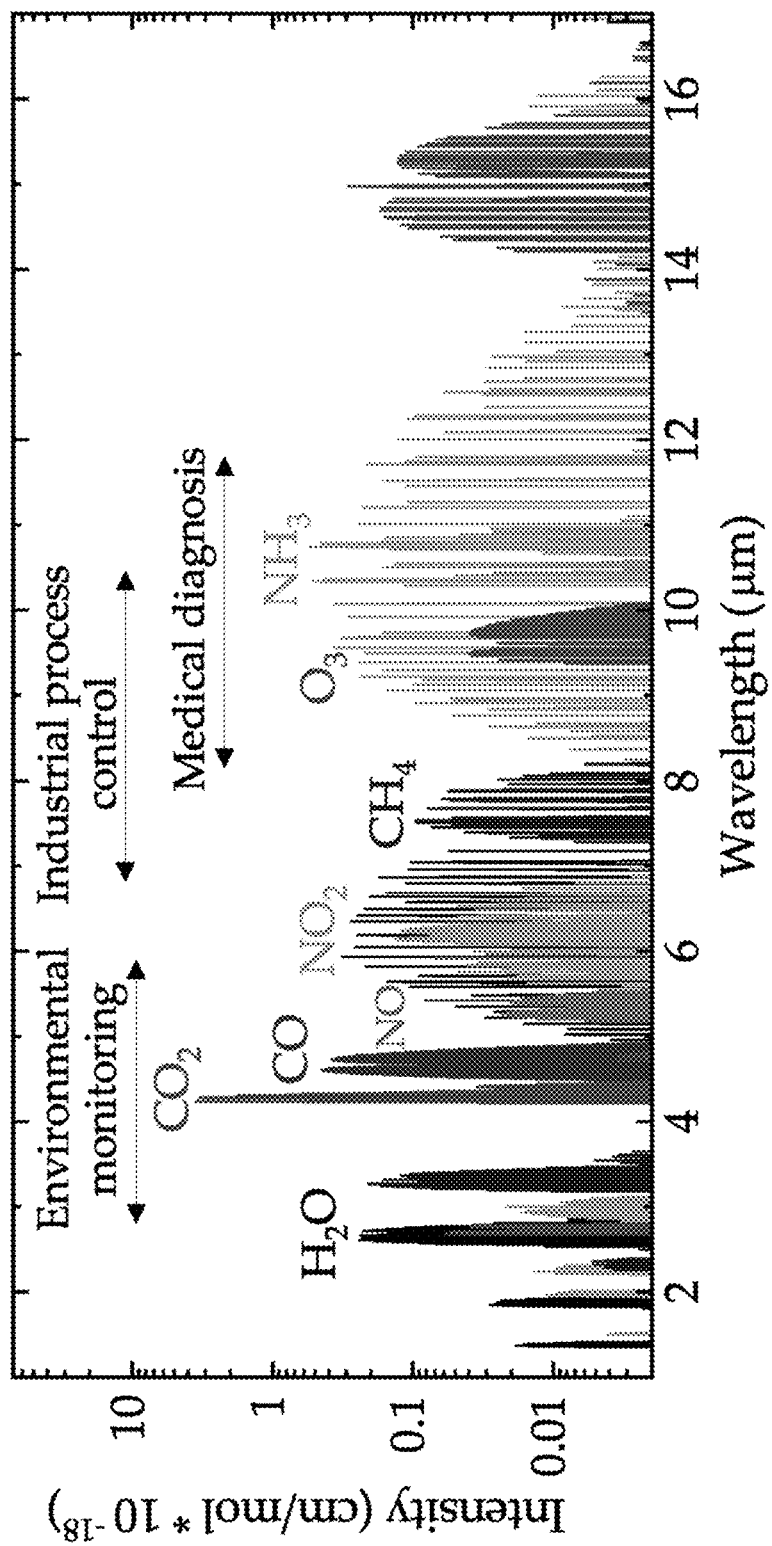
FIG. 4 shows a graph of some gasses at their peak absorption wavelengths.

FIG. 4 provides a depiction of some gasses at their peak absorption wavelengths. FIG. 4 further provides typical uses for detection of different gasses. The detector 42 may be a single or multi-channel infrared detector. The multi-channel infrared detectors may be two channel, four channel, or eight channel detectors. In a multi-channel detector, the filter 12a-d may be integrated with the detector. Each channel on the detector is capable of detecting a different wavelength in the IR spectrum. Thus, a single detector 42 may be able to detect multiple gasses without the need to change the filter.

The multi-channel detectors may be a pyroelectric detector. Pyroelectric crystals have a rare asymmetry due to their single polar axis. This causes their polarization to change with temperature. The pyroelectric effect used in sensor technology involves a thin pyroelectric crystal coated perpendicular to the polar axis with electrodes. On the upper electrode of the crystal, an absorbing layer, also termed a black layer, may be applied. When the absorbing layer interacts with infrared radiation, the pyroelectric layer heats up and a surface charge is formed. If the radiation is switched off, a charge of the opposite polarity forms. However, the level of the charge may be very low. Before the finite internal resistance of the crystal can equalize the charges, extremely low-noise and low leakage current field-effect transistors (JFET) or one or more operational amplifiers (OpAmps) may convert the charges into a signal voltage.

The above arrangement may be placed on a first circuit board. Other circuitry, including the JFETs or OpAmps, and a second sample tube containing a reference gas, may be placed on a piggybacked circuit board. This design choice increases the overall depth of the sensor package, but does not increase the length or width, thereby maintaining the footprint size of the sensor 10.

More specifically, the IR lamp may be moved back from the state-of-the-art placement at the first end portion of the sample tube. The IR lamp 22 of the present disclosure is moved away from the first section 16a of the sample tube in order to reduce the effects of heat generated by the IR lamp 22 on the first sample tube section 16a. In addition to moving the IR lamp 22 away from the first end portion 23 of the first sample tube section 16a, the IR lamp 22 may be connected to a heat sink which takes any excess heat generated by the IR lamp 22 and directs it away from the first sample tube section 16a. The first light pipe section 18 may direct the light of the IR lamp 22 toward the first sample tube section 16a. The light pipe material is known to transmit up to 90% of the light through the length of the light pipe material.

The above arrangement of component parts of the sensor 10 achieves the important result of reducing the transmission of heat from the IR lamp to the sample tube, which is an existing problem in the state-of-the-art. The heat generated by the IR lamp can heat the sample tube, and effect the operation of the thermopile in the sensor. Because the IR lamp 22 is physically spaced apart from the first sample tube section 16a, the heat is dissipated from the IR lamp 22, either to the surrounding air or to the heat sink before it reaches the first sample tube section 16a. The dissipation of heat before the heat reaches the first sample tube section 16a prevents negative effects to the thermopile.

In some embodiments, the heat dissipation feature may alone be used. That is, the IR lamp 22 may be moved from a first end portion of a sample tube, and a light pipe used to direct the light from the IR lamp in to the sample tube. Only a single section of sample tube may be used, because the first light pipe section is all that is required to decouple the heat of the IR lamp 22 from the sample tube. Thus, these embodiments do not have a second light pipe section or a second sample tube section.

However, other embodiments do include the second light pipe section 20 and the second sample tube section 16b. This is because the gas detection sensor 10 uses a principle known either as the Beer-Lambert Law. For purposes of this disclosure, the Beer-Lambert Law is given as:

$$I=I_o e^{-KLC}$$

Where I is the intensity of light at the detector, $I_o$ is the intensity of the light entering the sample, K is the molar absorptivity, L is the distance the light travels through the sample, and C is the concentration of the gas being tested for. Thus, the absorbance of the light is proportional to the distance the light travels through the sample. We can assume equal concentration because the gas is being tested for in the atmosphere and entropy is in effect, dispersing the tested for gas in an equal concentration, at least locally, in the atmosphere. Thus, there will be more absorption of the light with a longer sample tube. However, a long sample tube makes the sensor physically larger, and the state-of-the-art sensors are already almost too large for their desired applications.

If the sample tube may be split in to more than one section, the two sections may be placed in parallel. The placement of the two sections in parallel keeps the footprint of the sensor the same. While this creates a longer sample tube in the same footprint, it simultaneously creates a problem. The problem is that light from the IR lamp 22 cannot, on its own, curve after exiting the first section to enter the second section.

Sample tubes are designed with two apertures. A first aperture 38 may allow atmospheric gas in to the sample tube, and a second aperture 40 may allow gas to leave the sample tube. Thus, when split, each sample tube section would need a set of apertures in order for the sample tube section to obtain a sample.

A piece of light pipe may be placed between the two sections of sample tube in order to capture the light from the first section and direct the light to the second section. Specifically, a first end portion 28 of the curved second light pipe section 20 may be substantially located abutting a second end portion 30 of the first sample tube section 16a. A second end portion 32 of the curved second light pipe section 20 may be substantially located at a first end 34 of the second sample tube section 16b. Light pipe sections may be formed either straight or curved, rigid or flexible. This disclosure contemplates both rigid and flexible light pipes to direct the light from the second end portion 30 of a first sample tube section 16*a* to a first end 34 of the second sample tube section 16*b*.

In operation, the IR lamp 22 may be powered to emit light. The IR lamp 22 may be operated in such a way to chop or modulate the emission of light. This allows the detector to differentiate the radiation from the IR lamp 22 from the IR radiation present in the spectrum of atmospheric light. The light radiation from the IR lamp 22 is then directed in to and through the first light pipe section 18. With rare exception, at least 80%, and as much as 90% of the IR spectrum light from the IR lamp 22 is transmitted through the first light pipe section 18.

The IR spectrum light then enters the interior of the first sample tube section 16*a*. While passing through the first sample tube section 16*a*, the IR spectrum light will encounter the sample in the interior of the first sample tube section 16*a*. The sample may enter the interior though the first aperture 38. Some portion of the atmosphere adjacent to the first sample tube section 16*a* forms the sample in the interior 60 of the first sample tube section 16*a*. The sample may be continuously cycling through the interior of the first sample tube section 16*a* by cycling through the first aperture 38 and second aperture 40, which are both fluidly connected to the local atmosphere. If any of the one or more gases are present for which the sensor 10 is detecting, some amount of the IR spectrum light is absorbed in the first sample tube section 16*a* by those one or more gases. The IR spectrum light eventually reaches the second end portion 30 of the first sample tube section 16*a*.

After reaching the second end portion 30 of the first sample tube section 16*a*, the IR spectrum light enters the second light pipe section 20. The IR spectrum light enters the second light pipe section 20 at a first end portion 28. The IR spectrum light then travels through the second light pipe section 20 to a second end portion 32. Again, the light pipe transmits between 80% and 90% of the light that enters. Thus, the circuitry on the sensor 10, which may include one or more processors, and one or more memories will include instructions which account for this inefficiency in order to avoid false positive detections from the loss of some of the light at the observed wavelength due to light pipe transmission inefficiencies. The curvature of the light pipe material does not cause any further inefficiencies as compared to straight pieces of the light pipe material. Further, the flexible light pipe material does not cause any further inefficiencies than a rigid piece of light pipe material. Thus, the IR spectrum light which enters the second section of light pipe material travels through the light pipe and exists with a 10% to 20% loss of the IR spectrum light which entered the second light pipe section 20. At the second end portion 32 of the second light pipe section 20, the IR spectrum light enters the second sample tube section 16*b*.

The IR spectrum light enters the first end portion 34 of the second sample tube section 16*b*. At this point the intensity of the observed wavelength may have already been reduced by up to 40% due to the inefficiencies inherent in the first light pipe section 18 and second light pipe section 20 The intensity of the observed wavelength may be reduced even further than the reductions caused by the inefficiencies by the light pipe sections 18, 20 if there is a quantity of a gas which the senor is trying to detect present in the sample of the first sample tube section 16*a*. Again, the inefficiencies of the light pipe material are built in to the calculations performed by the system in detecting the presence of a gas, so these inefficiencies will not product false positive detections. The IR spectrum light traverses across the second section 16*b* of sample tube from a first end portion 34 to a second end portion 36. The filter 12 and the detector 42 may be attached to or abut the second end portion 36 of the second sample tube section 16*b*.

The sample in the second sample tube section 16*b* may be nearly identical to the sample in the first sample tube section 16*a*. This is because both samples are drawn from the atmosphere in the immediate vicinity of the sensor 10. Similar to the first sample tube section 16*a*, the sample may flow in and out through the first aperture 44 and the second aperture 46 in the second sample tube section 16*b*. Again, this allows continuous flow through the interior 62 the second sample tube section 16*b*, ensuring that if any of the one or more gasses the sensor 10 is detecting for is present in the atmosphere, the one or more gasses are also present in the sample. If any of the one or more gasses are present, then the one or more gasses may absorb light at the detection wavelength in the IR spectrum.

As shown in FIG. 3, after passing through the second sample tube section 16*b*, the IR spectrum light may arrive at the one or more filters 12*a-d*. As discussed above, the one or more filters may be a separate component, or the one or more filters may be integrated with the detector 42. Regardless of the physical location, the one or more filters 12*a-d* perform the same function. Specifically, as light arrives at the one or more filters 12*a-d*, the one or more filters 12*a-d* bandpass light in a narrow band centered on a detection wavelength which is absorbed by the gas the sensor is working to detect. If there is a multi-channel filter/detector combination, then each detector may have an individual filter 12*a-d*. For example, if the sensor 10 includes a four channel detector 42, as is shown in FIG. 3, then the detector may have a filter 12*a-d* for each channel. As discussed above, it is understood that the detector may be a one, two four, or eight channel detector, with a corresponding number of filters. Each filter will have different bandpass characteristics. Specifically, each filter will bandpass a band centered on a different detection wavelength. Each channel is therefore able to detect the presence of a different gas. After the IR spectrum light arrives at the detector, the light may cause an increase in current on the detector, as is described above. Through circuitry well known in the art, the signal may be amplified and converted to a voltage signal in order to determine if the detected IR spectrum light is indicative of the presence of one or more gasses.

After the detector makes the measurement of the amount of IR light at a wavelength reaching the detector, the detector passes a signal to circuitry for further processing. This circuitry is well known in the art and determines if the gas being detected is present in the sample. However, unlike state-of-the-art circuitry, the circuitry of the present disclosure may include a memory storing instructions or an algorithm which accounts for the loss of light due to the inefficiency in the first light pipe section and second light pipe section in determining the presence of a gas. The sensor is based on absorption of IR light at a particular wavelength by a gas the sensor is designed to detect the presence of. Because the light pipe does include some amount of inefficiency, the inefficiency is accounted for in an algorithm in order to prevent false positives.

Below are a number of example embodiments described above.

In a 1st Example, a sensor for detecting the presence of one or more gasses, comprising: an IR lamp which generates light in the IR spectrum; a first light pipe section having a first end portion and a second end portion, the first end portion abutting the IR lamp and the first light pipe section passing the light through from the first end portion to the second end portion; a first sample tube section receiving light from the first light pipe section, the first sample tube section having a first interior containing a first sample, the first sample including a mix of gases from the local atmosphere, the IR spectrum light passing through the interior of the first sample tube section to a second end portion of the first sample tube section; a second light pipe section having an arcuate shape so that a first end and a second end of the second light pipe section face the same direction, the first end portion of the second light pipe section located adjacent to a second end portion of the first sample tube section, the second light pipe section receiving the light at the second end portion of the first sample tube section and transmitting the light from the first end portion to a second end portion; a second sample tube section with a first end portion and a second end portion, the first end portion of the second sample tube section located adjacent to the second end portion of the second light pipe section, the first end portion of the second sample tube section receiving the light from the second end of the second light pipe section, the second sample tube section having a second interior containing a second sample, the second sample including the mix of gases from the local atmosphere, the light passing through the interior of the second sample tube section to a second end portion of the second sample tube section; a first filter located at the second end portion of the second sample tube section, the first filter bandpassing only a band of IR spectrum light centered on a wavelength indicative of the presence of a gas in the mix of gases from the local atmosphere; and a first detector located behind to the first filter, the detector detecting the amount of IR spectrum light in the band of IR spectrum light.

In a 2nd Example, the sensor of Example 1, wherein the second light pipe section is rigid.

In a 3rd Example, the sensor of any of Examples 1-2, wherein the second light pipe section is flexible.

In a 4th Example, the sensor of any of Examples 1-3, further comprising a second filter and second detector integrated with the first filter and first detector, the second filter filtering a different band of IR spectrum light than the first filter.

In a 5th Example, the sensor of any of Examples 1-4, further comprising a memory and a processor, the memory having instructions stored thereon and executed on the processor, the instructions accounting for the inefficiency of the first light pipe section and the second light pipe section.

In a 6th Example, the sensor of any of Examples 1-5, wherein the first filter and first detector are integrated in a single component.

In a 7th Example, the sensor of Example 4-6, wherein the first filter, first detector, second filter, and second detector are all integrated in a single component.

In a 8th Example, a method for detecting the presence of a gas in a sample, comprising: providing an IR lamp, the IR lamp generating light in the IR spectrum; directing the IR spectrum light in to a first interior of a first sample tube section, the first sample tube section including a second end portion, the first interior of the first sample tube section containing a first sample of a mix of gasses from the local atmosphere; transporting the IR spectrum light through a light pipe material; directing the IR spectrum light in to a second sample tube section placed in parallel with the first, the second sample tube section having a second interior, the second interior containing a second sample of a mix of gasses from the local atmosphere; and detecting a filtered band of the IR spectrum light, the filtered band being centered on a detection wavelength, a reduced amount of filtered IR spectrum light at the detection wavelength being indicative of the presence of a gas which absorbs IR spectrum light at the detection wavelength.

In a 9th Example, the method of Example 8, wherein the light pipe material is flexible.

In a 10th Example, the method of any of Examples 8-9, further comprising placing a second piece of light pipe material between the IR lamp and the first sample tube section, the second piece of light pipe material directing the IR spectrum light in to the first interior of the first sample tube section.

In a 11th Example, the method of any of Examples 8-10, wherein the IR spectrum light is filtered by a bandpass filter with the band centered on the detection wavelength.

In a 12th Example, the method of any of Examples 8-11, wherein the first sample tube section and second sample tube section are of substantially equal length.

In a 13th Example, a sensor for detecting the presence of one or more gasses, comprising: an IR lamp which generates light in the IR spectrum; a first sample tube section receiving light from the IR lamp, the first sample tube section having a first interior containing a first sample, the first sample including a mix of gases from the local atmosphere, the IR spectrum light passing through the interior of the first sample tube section to a second end portion of the first sample tube section; a flexible light pipe section including a first end portion and a second end portion, and having an arcuate shape so that a first end portion and a second end portion of the flexible light pipe section face the same direction, the first end portion of the flexible light pipe section located adjacent to a second end portion of the first sample tube section, the second light pipe section receiving the light at the second end portion of the first sample tube section and transmitting the light from the first end portion to the second end portion; a second sample tube section including a first end portion and a second end portion, the first end portion of the second sample tube section located adjacent to the second end portion of the second light pipe section, the first end portion of the second sample tube section receiving the light from the second end portion of the second light pipe section, the second sample tube section having a second interior containing a second sample, the second sample including the mix of gases from the local atmosphere, the light passing through the interior of the second sample tube section to a second end portion of the second sample tube section; a filter located at the second end portion of the second sample tube section, the filter bandpassing a band of IR spectrum light centered on a detection wavelength, the detection wavelength indicative of the presence of a gas in the mix of gases from the local atmosphere; and a detector located next to the filter, the detector detecting the amount of IR spectrum light at the detection wavelength.

In a 14th Example, the sensor of Example 13, further comprising a first light pipe section having a first end portion and a second end portion, the first end portion abutting the IR lamp and passing the light through from the first end portion to the second end portion.

In a 15th Example, the sensor of Example 14, wherein the first light pipe section is flexible.

In a 16th Example, the sensor of Example 14-15, wherein the first light pipe section is rigid.

In a 17th Example, the sensor of any of Examples 13-16, further comprising a second filter and second detector integrated with the first filter and first detector, the second filter filtering a different band of IR spectrum light than the first filter.

In a 18th Example, the sensor of any of Examples 13-17, wherein the first filter and first detector are integrated in a single component.

In a 19th Example, the sensor of Example 17-18, wherein the first filter, first detector, second filter, and second detector are integrated in a single component.

In a 20th Example, the sensor of Example 19, wherein the first detector provides data for detecting a first gas, and the second detector provides data for a second gas.

The above description is given by way of example, and not limitation. Given the above disclosure, one skilled in the art could devise variations that are within the scope and spirit of the invention disclosed herein, including various ways of configuring the filters and detectors. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A sensor for detecting the presence of one or more gasses, comprising:
    an IR lamp which generates light in the IR spectrum;
    a first light pipe section having a first end portion and a second end portion, the first end portion abutting the IR lamp and the first light pipe section passing the light through from the first end portion to the second end portion;
    a first sample tube section receiving light from the first light pipe section, the first sample tube section having a first interior containing a first sample, the first sample including a mix of gases from the local atmosphere, the IR spectrum light passing through the interior of the first sample tube section to a second end portion of the first sample tube section;
    a second light pipe section having an arcuate shape so that a first end and a second end of the second light pipe section face the same direction, the first end portion of the second light pipe section located adjacent to a second end portion of the first sample tube section, the second light pipe section receiving the light at the second end portion of the first sample tube section and transmitting the light from the first end portion to a second end portion;
    a second sample tube section with a first end portion and a second end portion, the first end portion of the second sample tube section located adjacent to the second end portion of the second light pipe section, the first end portion of the second sample tube section receiving the light from the second end of the second light pipe section, the second sample tube section having a second interior containing a second sample, the second sample including the mix of gases from the local atmosphere, the light passing through the interior of the second sample tube section to a second end portion of the second sample tube section;
    a first filter located at the second end portion of the second sample tube section, the first filter bandpassing only a band of IR spectrum light centered on a wavelength indicative of the presence of a gas in the mix of gases from the local atmosphere; and
    a first detector located behind to the first filter, the detector detecting the amount of IR spectrum light in the band of IR spectrum light.

2. The sensor of claim 1, wherein the second light pipe section is rigid.

3. The sensor of claim 1, wherein the second light pipe section is flexible.

4. The sensor of claim 1, further comprising a second filter and second detector integrated with the first filter and first detector, the second filter filtering a different band of IR spectrum light than the first filter.

5. The sensor of claim 1, further comprising a memory and a processor, the memory having instructions stored thereon and executed on the processor, the instructions accounting for the inefficiency of the first light pipe section and the second light pipe section.

6. The sensor of claim 1, wherein the first filter and first detector are integrated in a single component.

7. The sensor of claim 4, wherein the first filter, first detector, second filter, and second detector are all integrated in a single component.

8. A method for detecting the presence of a gas in a sample, comprising:
    providing an IR lamp, the IR lamp generating light in the IR spectrum;
    directing the IR spectrum light in to a first interior of a first sample tube section, the first sample tube section including a second end portion, the first interior of the first sample tube section containing a first sample of a mix of gasses from the local atmosphere;
    transporting the IR spectrum light through a light pipe material;
    directing the IR spectrum light in to a second sample tube section placed in parallel with the first, the second sample tube section having a second interior, the second interior containing a second sample of a mix of gasses from the local atmosphere; and
    detecting a filtered band of the IR spectrum light, the filtered band being centered on a detection wavelength, a reduced amount of filtered IR spectrum light at the detection wavelength being indicative of the presence of a gas which absorbs IR spectrum light at the detection wavelength.

9. The method of claim 8, wherein the light pipe material is flexible.

10. The method of claim 8, further comprising placing a second piece of light pipe material between the IR lamp and the first sample tube section, the second piece of light pipe material directing the IR spectrum light in to the first interior of the first sample tube section.

11. The method of claim 8, wherein the IR spectrum light is filtered by a bandpass filter with the band centered on the detection wavelength.

12. The method of claim 8, wherein the first sample tube section and second sample tube section are of substantially equal length.

13. A sensor for detecting the presence of one or more gasses, comprising:
    an IR lamp which generates light in the IR spectrum;
    a first sample tube section receiving light from the IR lamp, the first sample tube section having a first interior containing a first sample, the first sample including a mix of gases from the local atmosphere, the IR spectrum light passing through the interior of the first sample tube section to a second end portion of the first sample tube section;
    a flexible light pipe section including a first end portion and a second end portion, and having an arcuate shape so that a first end portion and a second end portion of the flexible light pipe section face the same direction, the first end portion of the flexible light pipe section located adjacent to a second end portion of the first sample tube section, the second light pipe section receiving the light at the second end portion of the first sample tube section and transmitting the light from the first end portion to the second end portion;

a second sample tube section including a first end portion and a second end portion, the first end portion of the second sample tube section located adjacent to the second end portion of the second light pipe section, the first end portion of the second sample tube section receiving the light from the second end portion of the second light pipe section, the second sample tube section having a second interior containing a second sample, the second sample including the mix of gases from the local atmosphere, the light passing through the interior of the second sample tube section to a second end portion of the second sample tube section;

a filter located at the second end portion of the second sample tube section, the filter bandpassing a band of IR spectrum light centered on a detection wavelength, the detection wavelength indicative of the presence of a gas in the mix of gases from the local atmosphere; and a detector located next to the filter, the detector detecting the amount of IR spectrum light at the detection wavelength.

14. The sensor of claim 13, further comprising a first light pipe section having a first end portion and a second end portion, the first end portion abutting the IR lamp and passing the light through from the first end portion to the second end portion.

15. The sensor of claim 14, wherein the first light pipe section is flexible.

16. The sensor of claim 14, wherein, the first light pipe section is rigid.

17. The sensor of claim 13, further comprising a second filter and second detector integrated with the first filter and first detector, the second filter filtering a different band of IR spectrum light than the first filter.

18. The sensor of claim 13, wherein the first filter and first detector are integrated in a single component.

19. The sensor of claim 17, wherein the first filter, first detector, second filter, and second detector are integrated in a single component.

20. The sensor of claim 19, wherein the first detector provides data for detecting a first gas, and the second detector provides data for a second gas.

* * * * *